United States Patent
Takakuwa et al.

(10) Patent No.: US 10,173,952 B2
(45) Date of Patent: Jan. 8, 2019

(54) METHOD FOR PRODUCING CHLOROPROPENE AND METHOD FOR PRODUCING 2,3,3,3-TETRAFLUOROPROPENE

(71) Applicant: DAIKIN INDUSTRIES, LTD., Osaka (JP)

(72) Inventors: Tatsuya Takakuwa, Osaka (JP); Kazuhiro Takahashi, Osaka (JP); Daisuke Karube, Osaka (JP); Takehiro Chaki, Osaka (JP); Masayuki Kishimoto, Osaka (JP); Yuzo Komatsu, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 15/324,827

(22) PCT Filed: Jun. 16, 2015

(86) PCT No.: PCT/JP2015/067326
§ 371 (c)(1),
(2) Date: Jan. 9, 2017

(87) PCT Pub. No.: WO2016/009774
PCT Pub. Date: Jan. 21, 2016

(65) Prior Publication Data
US 2017/0217859 A1  Aug. 3, 2017

(30) Foreign Application Priority Data

Jul. 15, 2014  (JP) ................................ 2014-145424

(51) Int. Cl.
| | | |
|---|---|---|
| C07C 17/25 | (2006.01) | |
| C07C 17/20 | (2006.01) | |
| C07C 17/383 | (2006.01) | |
| C07C 21/18 | (2006.01) | |
| C01B 7/19 | (2006.01) | |
| B01J 23/26 | (2006.01) | |
| B01D 3/14 | (2006.01) | |

(52) U.S. Cl.
CPC ............. *C07C 17/25* (2013.01); *B01D 3/143* (2013.01); *B01J 23/26* (2013.01); *C01B 7/195* (2013.01); *C01B 7/196* (2013.01); *C07C 17/206* (2013.01); *C07C 17/383* (2013.01); *Y02P 20/582* (2015.11)

(58) Field of Classification Search
CPC ..... C07C 17/087; C07C 17/10; C07C 17/206; C07C 17/25; C07C 17/383; C07C 21/18; C07C 19/10
See application file for complete search history.

(56) References Cited

U.S. PATENT DOCUMENTS

| | | | |
|---|---|---|---|
| 2,996,555 A | 8/1961 | Rausch et al. | |
| 2011/0207975 A9* | 8/2011 | Merkel | .................. C01B 7/035 570/160 |
| 2015/0080619 A1 | 3/2015 | Deur-Bert et al. | |
| 2016/0237009 A1 | 8/2016 | Deur-Bert et al. | |

FOREIGN PATENT DOCUMENTS

| | | |
|---|---|---|
| WO | 2008/002499 | 1/2008 |
| WO | 2008/040969 | 4/2008 |
| WO | 2013/015068 | 1/2013 |
| WO | 2013/114015 | 8/2013 |

OTHER PUBLICATIONS

International Search Report dated Sep. 1, 2015 in International (PCT) Application No. PCT/JP2015/067326.
Extended European Search Report dated Feb. 12, 2018 in European Application No. 15821671.3.

* cited by examiner

*Primary Examiner* — Jafar F Parsa
(74) *Attorney, Agent, or Firm* — Wenderoth, Lind & Ponack, L.L.P.

(57) ABSTRACT

This invention provides a method for stably producing 2,3,3,3-tetrafluoropropene for a long period of time wherein unreacted materials are reused after distillation without liquid-liquid separation to suppress catalyst deactivation. The method for producing 2,3,3,3-tetrafluoropropene comprises the step of reacting 1233xf or like chloropropene with hydrogen fluoride in the presence of a catalyst, the step of subjecting the reaction mixture obtained in the above step to distillation to separate the mixture into a first stream comprising 2,3,3,3-tetrafluoropropene as a main component and a second stream comprising unreacted hydrogen fluoride and organic matter containing unreacted chloropropene as main components, and the step of recycling the second stream to the above reaction, the distillation being performed under conditions in which the unreacted hydrogen fluoride and the organic matter containing the unreacted chloropropene do not undergo liquid-liquid separation at a portion of a distillation column from which the second stream is withdrawn.

2 Claims, 4 Drawing Sheets

_US 10,173,952 B2_

METHOD FOR PRODUCING CHLOROPROPENE AND METHOD FOR PRODUCING 2,3,3,3-TETRAFLUOROPROPENE

TECHNICAL FIELD

The present invention relates to a method for producing 2,3,3,3-tetrafluoropropene that can be used as a refrigerant or the like, and a method for producing a chloropropene that can be used for the production of 2,3,3,3-tetrafluoropropene.

BACKGROUND ART

Alternative refrigerants such as HFC-125($C_2HF_5$) and HFC-32($CH_2F_2$) have been widely used as important replacements for CFC, HCFC, etc., which cause ozone layer depletion. However, these alternative refrigerants are potent global warming substances, thus creating concern that diffusion of the refrigerants would increase global warming. As a preventive measure, these refrigerants are recovered after use. However, complete recovery of the refrigerants is impossible. In addition, diffusion of these refrigerants due to, for example, leakage cannot be ignored. The use of $CO_2$ or hydrocarbon-based substances as alternative refrigerants has also been investigated. However, because $CO_2$ refrigerants have low efficiency and devices using such refrigerants inevitably become large, $CO_2$ refrigerants have many problems in terms of the overall reduction of greenhouse gas emissions, including energy to be consumed. Furthermore, hydrocarbon-based substances pose safety problems due to their high flammability.

HFO-1234yf ($CF_3CF=CH_2$), which is an olefinic HFC with low global warming potential, has recently been attracting attention as a material to solve the above problems. HFO-1234yf, used alone or in combination with other substances, such as hydrofluorocarbons (HFCs), hydrofluoroolefins (HFOs), and hydrochlorofluoroolefins (HCFOs), is expected to be useful as a refrigerant, and additionally as a blowing agent, propellant, extinguishing agent, or the like.

Various methods are known for producing HFO-1234yf. For example, there have been proposed methods such as a method in which $CCl_3CF_2CH_3$ as a starting material is reacted with hydrogen fluoride (HF) that has an amount exceeding the stoichiometric amount (Patent Literature 1), and a method in which a fluorocarbon represented by $CF_3CFHCFH_2$ is subjected to dehydrofluorination treatment (Patent Literature 2).

CITATION LIST

Patent Literature

PTL 1: US Patent Application Publication No. 2996555
PTL 2: WO2008/002499

SUMMARY OF INVENTION

Technical Problem

In the production methods disclosed in the Patent Literature mentioned above, the conversion of HCFO-1233xf to HFO-1234yf is as low as 20% or less. Additionally, the outflow from the reactor contains not only the desired product HFO-1234yf, but also a mixture containing the unreacted HCFO-1233xf and HF in an amount at least equimolar to that of the unreacted HCFO-1233xf. Thus, by distillation treatment, the desired HFO-1234yf is withdrawn from the top of the distillation column, and other components, i.e., HF and HCFO-1233xf, are withdrawn from the bottom of the distillation column and recycled by feeding HF and HCFO-1233xf again to the reactor. However, depending on the molar ratio of HF and HCFO-1233xf or the still temperature, HF and HCFO-1233xf may undergo liquid-liquid separation in the still. As a result, a high concentration of an organic phase at the lower phase is fed to the reactor. Such a high concentration of the organic phase fed to the reactor poses a problem of deactivation of the catalyst caused by the action of the organic matter.

The present invention has been accomplished in view of the above. An object of the present invention is to provide a method for stably producing 2,3,3,3-tetrafluoropropene for a long period of time in which unreacted materials are reused after distillation without liquid-liquid separation to suppress catalyst deactivation. Another object of the present invention is to provide a method for stably producing a chloropropene used for the production of 2,3,3,3-tetrafluoropropene for a long period of time in which unreacted materials are reused after distillation without liquid-liquid separation to suppress catalyst deactivation, as in the method for producing 2,3,3,3-tetrafluoropropene.

Solution to Problem

The present inventors conducted extensive research to achieve the above objects and found that the objects can be achieved by performing distillation under conditions in which unreacted materials including hydrogen fluoride and organic matter such as HCFO-1233xf as main components do not undergo liquid-liquid separation. The present invention has thus been accomplished.

Specifically, the present invention relates to the following method for producing a chloropropene and the following method for producing 2,3,3,3-tetrafluoropropene.

1. A method for producing a chloropropene represented by formula (II): $CX_3CCl=CH_2$, wherein at least one X is F and the other or others are Cl or F, and each X may be the same or different, from a starting material containing a chloropropane represented by formula (Ia): $CX_3CClYCH_2Y$, wherein X is Cl or F and each X may be the same or different, Y is H, F, or Cl and each Y may be the same or different and/or a chloropropene represented by formula (Ib): $CY_3CCl=CZ_2$, wherein Y is H or Cl and each Y may be the same or different, and Z is H, F, or Cl and each Z may be the same or different, the method comprising the following steps (a) to (c):
   (a) reacting the starting material with hydrogen fluoride in the presence of a catalyst;
   (b) subjecting the reaction mixture obtained in step (a) to distillation to separate the mixture into a first stream comprising the chloropropene of formula (II) as a main component and a second stream comprising unreacted starting material and unreacted hydrogen fluoride as main components; and
   (c) recycling the second stream separated in the above step to the reaction of step (a),
   the distillation of step (b) being performed under conditions in which the unreacted starting material and the unreacted hydrogen fluoride do not undergo liquid-liquid separation at a portion of a distillation column from which the second stream is withdrawn.
2. The method according to Item 1, wherein in the distillation of step (b), the molar ratio of the hydrogen fluoride to the starting material is 15 or more, and the pressure in the distillation column where the distillation of step (b) is performed is 0 MPa or more but 1 MPa or less.

3. A method for producing 2,3,3,3-tetrafluoropropene from a chloropropene represented by formula (II): $CX_3CCl=CH_2$, wherein at least one X is F and the other or others are Cl or F, and each X may be the same or different, the method comprising the following steps (d) to (f):

(d) reacting the chloropropene of formula (II) with hydrogen fluoride in the presence of a catalyst;

(e) subjecting the reaction mixture obtained in step (d) to distillation to separate the mixture into a first stream comprising 2,3,3,3-tetrafluoropropene as a main component and a second stream comprising unreacted hydrogen fluoride and organic matter containing unreacted chloropropene represented by formula (II) as main components; and (f) recycling the second stream separated in step (e) to the reaction of step (d), the distillation of step (e) being performed under conditions in which the unreacted hydrogen fluoride and the organic matter containing the unreacted chloropropene represented by formula (II) do not undergo liquid-liquid separation at a portion of a distillation column from which the second stream is withdrawn.

4. The method according to Item 3, wherein the chloropropene represented by formula (II) is 2-chloro-3,3,3-trifluoropropene, and the distillation of step (e) is performed under conditions that satisfy the relationship of the following equation (1):

$$Y \geq -0.00004X^5 + 0.0026X^4 - 0.0653X^3 + 0.8224X^2 - 5.3282X + 14.787 \quad (1)$$

wherein Y is the pressure in the distillation column where the distillation of step (e) is performed, and X is the molar ratio of the hydrogen fluoride to the organic matter.

5. The method according to Item 4, wherein the molar ratio X is 10 or more, and the pressure Y is 0 MPa or more but 1 MPa or less.

6. A method for producing 2,3,3,3-tetrafluoropropene, the method comprising:

a first stage of obtaining a chloropropene represented by formula (II): $CX_3CCl=CH_2$, wherein at least one X is F and the other or others are Cl or F, and each X may be the same or different, from a starting material containing a chloropropane represented by formula (Ia): $CX_3CClYCH_2Y$, wherein X is Cl or F and each X may be the same or different, Y is H, F, or Cl and each Y may be the same or different and/or a chloropropene represented by formula (Ib): $CY_3CCl=CZ_2$, wherein Y is H or Cl and each Y may be the same or different, Z is H, F, or Cl and each Z may be the same or different; and a second stage of obtaining 2,3,3,3-tetrafluoropropene from the chloropropene of formula (II), the first stage comprising the following steps (a) to (c):

(a) reacting the starting material with hydrogen fluoride in the presence of a catalyst;

(b) subjecting the reaction mixture obtained in step (a) to distillation to separate the mixture into a first stream comprising the chloropropene of formula (II) as a main component and a second stream comprising unreacted starting material and unreacted hydrogen fluoride as main components; and (c) recycling the second stream separated in step (b) to the reaction of step (a), the second stage comprising the following steps (d) to (f):

(d) reacting the chloropropene of formula (II) with hydrogen fluoride in the presence of a catalyst;

(e) subjecting the reaction mixture obtained in step (d) to distillation to separate the mixture into a first stream comprising 2,3,3,3-tetrafluoropropene as a main component and a second stream comprising unreacted hydrogen fluoride and organic matter containing unreacted chloropropene represented by formula (II) as main components; and (f) recycling the second stream separated in step (e) to the reaction of step (d), the distillation of step (b) being performed under conditions in which the unreacted starting material and the unreacted hydrogen fluoride do not undergo liquid-liquid separation, and/or the distillation of step (e) being performed under conditions in which the unreacted hydrogen fluoride and the organic matter containing the unreacted chloropropene represented by formula (II) do not undergo liquid-liquid separation.

7. The method according to Item 6, wherein the chloropropene represented by formula (II) is 2-chloro-3,3,3-trifluoropropene, and the distillation of step (e) is performed under conditions that satisfy the relationship of the following equation (1):

$$Y \geq -0.00004X^5 + 0.0026X^4 - 0.0653X^3 + 0.8224X^2 - 5.3282X + 14.787 \quad (1)$$

wherein Y is the pressure in the distillation column where the distillation of step (e) is performed, and X is the molar ratio of the hydrogen fluoride to the organic matter.

8. The method according to Item 7, wherein the molar ratio X is 10 or more, and the pressure Y is 0 MPa or more but 1 MPa or less.

9. The method according to any one of Items 6 to 8, wherein the starting material is 1,1,1,2,3-pentachloropropane, the molar ratio of the hydrogen fluoride to the 1,1,1,2,3-pentachloropropane in the distillation of step (b) is 15 or more, and the pressure in the distillation column where the distillation of step (b) is performed is 0 MPa or more but 1 MPa or less.

Advantageous Effects of Invention

In the production of a chloropropene in the present invention, distillation is performed under conditions in which a mixture containing the unreacted starting material and unreacted hydrogen fluoride that remain after a reaction of the starting material do not undergo liquid-liquid separation, and a fraction obtained by the distillation is reused in the reaction. Thus, catalyst deactivation in the reaction system can be suppressed, enabling the chloropropene to be stably produced for a long period of time.

Moreover, in the production of 2,3,3,3-tetrafluoropropene in the present invention, distillation is performed under conditions in which a mixture containing the unreacted raw material and unreacted hydrogen fluoride that remain after a reaction of the raw material do not undergo liquid-liquid separation, and a fraction obtained by the distillation is reused in the reaction. Thus, catalyst deactivation in the reaction system can be suppressed, enabling 2,3,3,3-tetrafluoropropene to be stably produced for a long period of time.

DESCRIPTION OF EMBODIMENTS

Figure 1:
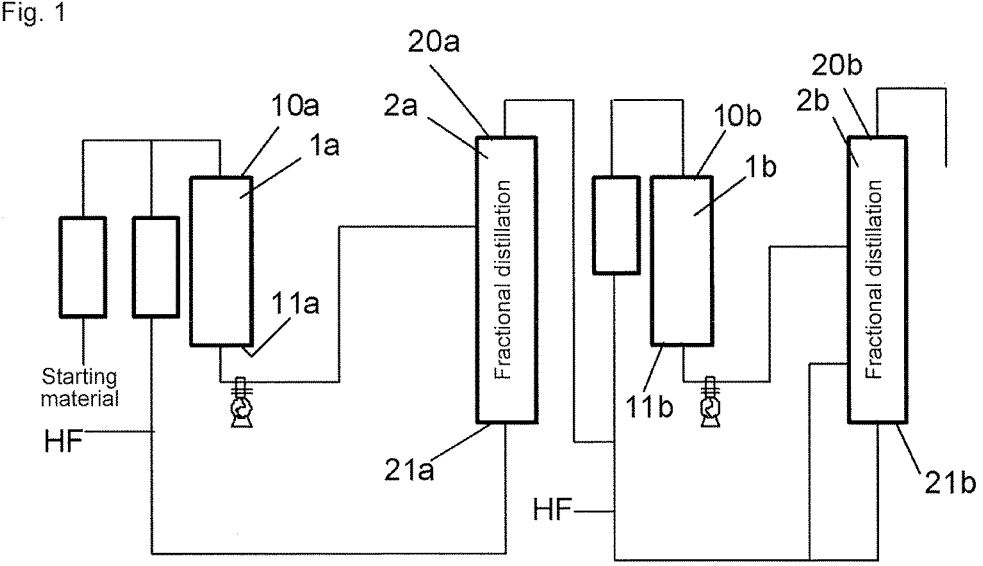
FIG. 1 is a flow diagram illustrating an example of the method for producing 2,3,3,3-tetrafluoropropene.

Embodiments of the present invention are described in detail below.

Method for Producing Chloropropene

The chloropropene is represented by formula (II): $CX_3CCl=CH_2$, wherein at least one X is F and the other or others are Cl or F, and each X may be the same or different. This chloropropene is produced from a starting material containing a chloropropane represented by formula (Ia): $CX_3CClYCH_2Y$, wherein X is Cl or F and each X may be the same or different, Y is H, F, or Cl and each Y may be the same or different, and/or a chloropropene represented by formula (Ib): $CY_3CCl=CZ_2$, wherein Y is H or Cl and each Y may be the same or different, Z is H, F, or Cl and each Z may be the same or different.

Hereinafter, the chloropropane represented by formula (Ia) may be referred to as "starting material chloropropane," the chloropropene represented by formula (Ib) may be referred to as "starting material chloropropene," and the chloropropene represented by formula (II) may be referred to as "chloropropene intermediate." "Starting material chloropropane" and "starting material chloropropene" may be collectively referred to as "starting material." "Starting material" means either "starting material chloropropane" or "starting material chloropropene," or both.

Hereinafter, the stage of producing a chloropropene represented by formula (II) (chloropropene intermediate) from the starting material mentioned above is referred to as "first stage."

Specific examples of the starting material chloropropane of formula (Ia) include $CCl_3CHClCH_2Cl$ (which hereinafter may be referred to as "240db"), $CF_3CHClCH_2Cl$ (which hereinafter may be referred to as "243db"), $CF_3CClFCH_3$ (which hereinafter may be referred to as "244bb"), $CF_3CHClCH_2F$ (which hereinafter may be referred to as "244db"), $CFCl_2CHClCH_2Cl$ (which hereinafter may be referred to as "241db"), $CF_2ClCHClCH_2Cl$ (which hereinafter may be referred to as "242dc"), and the like. Among these, 240db (1,1,1,2,3-pentachloropropane), 243db (2,3-dichloro-1,1,1-trifluoropropane), and 244bb (2-chloro-1,1,1,2-tetrafluoropropane) are particularly preferable. The starting material chloropropanes may be used singly or in a combination of two or more.

Specific examples of the starting material chloropropene of formula (Ib) include 1,1,2,3-tetrachloropropene ($CCl_2=CClCH_2Cl$, which hereinafter may be referred to as "1230xa") and 2,3,3,3-tetrachloropropene ($CH_2=CClCCl_3$, which hereinafter may be referred to as "1230xf").

Specific examples of the chloropropene intermediate of formula (II) include 2-chloro-3,3,3-trifluoropropene ($CF_3CCl=CH_2$, which hereinafter may be referred to as "HCFO-1233xf" or "1233xf"), 1,2-dichloro-1,1-difluoro-3-propene ($CClF_2CCl=CH_2$, which hereinafter may be referred to as "1232xf"), and 1,1,2-trichloro-1-fluoro-3-propene ($CCl_2FCCl=CH_2$, which hereinafter may be referred to as "1231xf").

The first stage comprises the following steps (a) to (c):
(a) reacting the starting material with hydrogen fluoride in the presence of a catalyst;
(b) subjecting the reaction mixture obtained in step (a) to distillation to separate the mixture into a first stream comprising the chloropropene of formula (II) as a main component and a second stream comprising the unreacted starting material and the unreacted hydrogen fluoride as main components; and
(c) recycling the second stream separated in step (b) to the reaction of step (a).

In particular, in the present invention, the distillation of step (b) is performed under conditions in which the unreacted starting material and the unreacted hydrogen fluoride do not undergo liquid-liquid separation at a portion of the distillation column from which the second stream is withdrawn.

In step (a), the starting material is reacted with hydrogen fluoride to obtain a product containing a chloropropene intermediate. The product containing a chloropropene intermediate is a compound that serves as an intermediate in the production of 2,3,3,3-tetrafluoropropene.

The method for reacting the starting material with hydrogen fluoride in the presence of a catalyst is not particularly limited. Examples of specific embodiments of the method include a method in which a catalyst is placed in a tubular flow reactor, and the starting material and hydrogen fluoride are introduced into the reactor.

The starting material can be reacted with hydrogen fluoride in a gas phase. The starting material and hydrogen fluoride are brought into contact with each other in a gaseous state in the reaction temperature region described below. When the starting material is liquid at an ordinary temperature and ordinary pressure, the starting material may be evaporated using an evaporator and supplied to a reactor where the reaction of step (a) is performed.

Hydrogen fluoride may generally be supplied to a reactor in a gas phase together with the starting material. The amount of hydrogen fluoride supplied is generally about 1 to 100 moles, preferably about 5 to 50 moles, and more preferably about 15 to 40 moles, per mole of the starting material. By setting the amount within such a range, the conversion of the starting material can be maintained within a desirable range. An amount of hydrogen fluoride of 15 moles or more per mole of the starting material is particularly preferable because deactivation of the catalyst can be suppressed.

The molar ratio of hydrogen fluoride and the starting material can be adjusted by the amounts of hydrogen fluoride and the starting material supplied to the reactor. Thus, regarding a stream not for recycling but for supplying the major raw materials to the reactor and the second stream, the flow rates of hydrogen fluoride and the starting material can be adjusted by additionally supplying hydrogen fluoride and the starting material or withdrawing them from the reactor.

Hydrogen fluoride and the starting material may be supplied to the reactor together with gas that is inert to the raw materials and the catalyst, such as nitrogen, helium, or argon. The concentration of inert gas may be about 0 to 10 mol % based on the total amount of the raw materials including the starting material and hydrogen fluoride introduced into the reactor and the inert gas, plus, when added, oxygen gas described later.

The starting material may be supplied to the reactor of step (a) together with oxygen or chlorine. In this case, the amount of oxygen or chlorine supplied may be about 0.1 to 50 mol % based on the total amount of the raw materials and oxygen, plus, when added, inert gas or based on the total amount of the raw materials and chlorine, plus, when added, inert gas. A large amount of oxygen or chlorine supplied is not preferred because a side reaction, such as oxidation reaction, occurs, resulting in a decrease in selectivity.

As a catalyst, known materials that have been used for this reaction can be used, and the type of catalyst is not particularly limited. For example, known catalysts usable in the dehydrohalogenation reaction can be used. Examples thereof include halides and oxides of transition metals, Group 14 and 15 elements, etc. Specific examples of transition elements include Ti, V, Cr, Mn, Fe, Co, Ni, Cu, Zn, Zr, Nb, Ta, W, and the like. Specific examples of Group 14 elements include Sn, Pb, and the like. Specific examples of Group 15 elements include Sb, Bi, and the like. Examples of halides of these elements include fluoride, chloride, and the like. These catalysts may be used singly or in a combination of two or more and may be supported on a carrier. Examples of carriers include, but are not particularly limited to, porous alumina silicate typified by zeolite, aluminum oxide, silicon oxide, activated carbon, titanium oxide, zirconia oxide, zinc oxide, aluminum fluoride, and the like. These may be used singly or in a combination of two or more, or a structural composite form thereof.

The reactor is preferably a tubular reactor. The method for bringing into contact with the catalyst is preferably a method using a fixed layer. The reactor is preferably made of a material resistant to the corrosive action of hydrogen fluoride, such as Hastelloy (registered trademark), Inconel (registered trademark), or Monel (registered trademark).

In the reaction of step (a), the reaction temperature is not particularly limited and is generally preferably about 200° C. to 550° C. When the temperature is in this range, excellent conversion of the starting material is exhibited, and the production of by-products caused by decomposition of the raw materials can be suppressed. The reaction temperature is more preferably about 300° C. to 450° C.

The pressure during the reaction of step (a) is not particularly limited, and the reaction may be performed under reduced pressure, ordinary pressure, or increased pressure. Although the reaction may be generally carried out at pressure near atmospheric pressure (0.1 MPa), it can also proceed smoothly under reduced pressure of less than 0.1 MPa. Further, the reaction may be performed under increased pressure within a range in which the raw materials do not liquefy.

There is no limitation on the reaction time. For example, the contact time represented by W/F0, i.e., the ratio of the amount of packed catalyst W(g) to the total flow rate F0 (a flow rate at 0° C. and 0.1 MPa: cc/sec) of gas components supplied to the reaction system is preferably about 0.1 to 90 g·sec/cc, and more preferably about 1 to 50 g·sec/cc. In this case, the total flow rate of gas components means the total flow rate of the starting material and hydrogen fluoride, and, when used, inert gas, oxygen, etc.

A reaction mixture containing a chloropropene intermediate, which is a product, as a main component and also containing the unreacted starting material and the unreacted hydrogen fluoride is obtained by performing step (a) described above.

In step (b), the reaction mixture obtained in step (a) is subjected to distillation. By this distillation, the mixture can be separated into a first stream comprising the chloropropene intermediate as a main component and a second stream comprising the unreacted starting material and the hydrogen fluoride as main components. The portion of the distillation column from which the second stream is withdrawn may be the still of the distillation column or a middle portion of the distillation column. The distillation can be performed using a distillation column commonly used or the like.

The distillation is performed under conditions in which the unreacted starting material and unreacted hydrogen fluoride that form the second stream do not undergo liquid-liquid separation. The liquid-liquid separation as used here refers to a state in which two or more liquids (for example, a liquid phase of chloropropane and a liquid phase of hydrogen fluoride) undergo separation into two phases, and does not refer to a state in which two or more liquids are mixed as a single liquid phase.

Examples of the method for performing distillation under conditions in which liquid-liquid separation does not occur include a method in which the molar ratio of the hydrogen fluoride to the unreacted starting material in the distillation column, i.e., the [the number of moles of the hydrogen fluoride]/[the number of moles of the unreacted starting material] value is adjusted. The molar ratio can be adjusted by additionally supplying or withdrawing the starting material and/or hydrogen fluoride to or from the distillation column or other lines. The phrase "the pressure in the distillation column" as used here refers to a gauge pressure (i.e., pressure in relation to atmospheric pressure taken as 0) unless otherwise stated.

Another method for performing distillation under conditions in which liquid-liquid separation does not occur is, for example, a method in which the pressure in the distillation column is adjusted. For instance, the pressure in the distillation column can be adjusted by changing the temperature in the distillation column. Alternatively, the pressure in the distillation column can be adjusted by supplying the reaction mixture, starting material, hydrogen fluoride, and/or others, such as inert gas, to the distillation column or discharging the reaction mixture, starting material, hydrogen fluoride, and/or others, such as inert gas.

The occurrence of liquid-liquid separation in the distillation column can be determined from the liquid density of a stream withdrawn from the distillation column. Specifically, when liquid-liquid separation occurs at a portion of the distillation column from which the second stream is withdrawn, an organic layer (layer containing the starting material), which is a lower layer, is mainly withdrawn from the distillation column; therefore, the liquid density of the stream withdrawn from the distillation column is higher than when liquid-liquid separation does not occur, and becomes a value close to the liquid density of the starting material alone. When such a change in the liquid density is observed, it can be determined that liquid-liquid separation has occurred.

The pressure in the distillation column is not particularly limited. For example, the pressure in the distillation column may be 0 to 1 MPa.

As described above, distillation is performed under conditions in which the unreacted starting material and the hydrogen fluoride do not undergo liquid-liquid separation, and the second stream containing the unreacted starting material and the unreacted hydrogen fluoride is withdrawn from the distillation column. If the second stream is withdrawn from the still of the distillation column, the temperature of the still can be, for example, as follows: when the pressure in the liquid-liquid separation curve of 1233xf-HF is 0.34 MPa (absolute pressure), the still can be heated to 33°

C. or more, which makes liquid-liquid separation much less likely to occur. The temperature of the still is particularly preferably 50° C. or more.

In step (c), the second stream withdrawn from the distillation column is fed to the reactor where the reaction of step (a) is performed. Thus, the unreacted starting material and the unreacted hydrogen fluoride can be recycled to the reaction of step (a). For example, the second stream can be fed to the reactor while pressure is applied with a pump, a compressor, or the like.

More specifically, conditions for the distillation can be set as follows.

First, the pressure in the distillation column where the distillation of step (b) is performed is defined as $Y_1$ (MPa; gauge pressure), the molar ratio of the hydrogen fluoride to the unreacted starting material (i.e., [the number of moles of the hydrogen fluoride]/[the number of moles of the unreacted starting material]) is defined as $X_1$, and the relationship between $X_1$ and $Y_1$ is plotted. For example, the relationship between $X_1$ and $Y_1$ (10 to 50 points) is plotted in the $Y_1$ range of 0 to 1 MPa and the $X_1$ range of 5 to 25. By plotting in such a manner, an X—Y curve is drawn, and a relational expression that expresses $Y_1$ as a function of $X_1$ is calculated from this curve. Automated calculation software may be used to calculate this relational expression.

If the relational expression is expressed as $f(X_1)$, as long as the relationship of $Y_1 \geq f(X_1)$ is satisfied, the distillation can be performed under conditions in which liquid-liquid separation does not occur. Thus, the molar ratio $X_1$ and the pressure in the distillation column $Y_1$ can be adjusted so to satisfy this relationship to perform the distillation.

As described above, withdrawing the second stream without occurrence of liquid-liquid separation in the distillation of step (b) prevents a high concentration of the unreacted starting material in the second stream, resulting in suppression of deactivation of the catalyst used in the reaction of step (a). If liquid-liquid separation into two phases occurs, the lower phase is the unreacted starting material, which has a greater specific gravity. Thus, if the second stream in a state in which liquid-liquid separation occurs is withdrawn, the unreacted starting material is recycled in a high concentration to the reactor. If the amount of such organic matter (unreacted starting material) is too large in the reaction system, the catalyst tends to be covered with the organic matter, leading to deactivation of the catalyst. However, withdrawing the second stream without occurrence of liquid-liquid separation in step (b) prevents a high concentration of the unreacted starting material from being fed to the reactor as described above, making deactivation of the catalyst unlikely to occur. This enables the chloropropene intermediate to be stably produced for a long period of time.

Method for Producing 2,3,3,3-tetrafluoropropene 2,3,3,3-tetrafluoropropene (which hereinafter may be referred to as "HFO-1234yf" or "1234yf") is produced using a chloropropene represented by formula (II): $CX_3CCl=CH_2$, wherein at least one X is F and the other or others are Cl or F, and each X may be the same or different (i.e., which corresponds to the chloropropene intermediate of the first stage) as a raw material.

Hereinafter, the stage of producing HFO-1234yf from the chloropropene intermediate is referred to as "second stage."

The second stage comprises the following steps (d) to (f):
(d) reacting the chloropropene of formula (II) with hydrogen fluoride in the presence of a catalyst;
(e) subjecting the reaction mixture obtained in step (d) to distillation to separate the mixture into a first stream comprising 2,3,3,3-tetrafluoropropene as a main component and a second stream comprising the unreacted hydrogen fluoride and organic matter containing the unreacted chloropropene represented by formula (II) as main components; and
(f) recycling the second stream separated in step (e) to the reaction of step (d).

In particular, in the present invention, the distillation of step (e) is performed under conditions in which the unreacted chloropropene intermediate and the unreacted hydrogen fluoride do not undergo liquid-liquid separation at a portion of the distillation column from which the second stream is withdrawn.

In step (d), the chloropropene intermediate is reacted with hydrogen fluoride to obtain the desired HFO-1234yf (2,3,3,3-tetrafluoropropene).

The method for reacting the chloropropene intermediate with hydrogen fluoride in the presence of a catalyst is not particularly limited. Examples of specific embodiments of the method include a method in which a catalyst is placed in a tubular flow reactor, and the chloropropene intermediate and hydrogen fluoride used as raw materials are introduced into the reactor.

The chloropropene intermediate can be reacted with hydrogen fluoride in a gas phase. The chloropropene intermediate and hydrogen fluoride are brought into contact with each other in a gaseous state in the reaction temperature region described below. When the chloropropene intermediate is liquid at an ordinary temperature and ordinary pressure, the chloropropene intermediate may be evaporated using an evaporator and supplied to a reactor where the reaction of step (d) is performed.

Hydrogen fluoride may be supplied to the reactor, for example, in the same manner as in step (a), and the method is not particularly limited. The amount of hydrogen fluoride supplied is generally about 1 to 100 moles, and preferably about 5 to 50 moles, per mole of the chloropropene intermediate. By setting the amount with such a range, the conversion of the chloropropene intermediate can be maintained within a desirable range. An amount of hydrogen fluoride of 10 moles or more per mole of the chloropropene intermediate is particularly preferable because deactivation of the catalyst can be suppressed.

The molar ratio of hydrogen fluoride and the chloropropene intermediate can be adjusted by the amounts of hydrogen fluoride and the chloropropene intermediate supplied to the reactor. Thus, for a stream for supplying the major raw materials to the reactor and the second stream, the flow rates of hydrogen fluoride and the starting material can be adjusted by additionally supplying these materials or withdrawing them from the reactor.

Hydrogen fluoride and the chloropropene intermediate may be supplied to the reactor together with gas that is inert to the raw materials and the catalyst, such as nitrogen, helium, or argon. The concentration of inert gas may be about 0 to 80 mol % based on the total amount of the raw materials including the chloropropene intermediate and hydrogen fluoride introduced into the reactor and the inert gas, plus, when added, oxygen gas described later.

The chloropropene intermediate may be supplied to the reactor of step (d) together with oxygen. In this case, the amount of oxygen supplied may be about 0.1 to 50 mol % based on the total amount of the raw materials and oxygen, plus, when added, inert gas. A large amount of oxygen supplied is not preferred because a side reaction, such as oxidation reaction, occurs, resulting in a decrease in selectivity.

As a catalyst, known materials that have been used for this reaction can be used, and the type of catalyst is not particularly limited. For example, the catalysts mentioned above as usable in step (a) can also be used in step (d).

The reactor is preferably a tubular reactor. The method for bringing into contact with the catalyst is preferably a method using a fixed layer. The reactor is preferably made of a material resistant to the corrosive action of hydrogen fluoride, such as Hastelloy (registered trademark), Inconel (registered trademark), or Monel (registered trademark).

In the reaction of step (d), the reaction temperature is not particularly limited and is generally preferably about 200° C. to 550° C. When the temperature is in this range, excellent conversion of the chloropropene intermediate into the desired product is exhibited, and the production of by-products caused by decomposition of the raw materials can be suppressed. The reaction temperature is more preferably about 300° C. to 450° C.

The pressure during the reaction of step (d) is not particularly limited, and the reaction may be performed under reduced pressure, ordinary pressure, or increased pressure. Although the reaction may be generally carried out at pressure near atmospheric pressure (0.1 MPa), it can also proceed smoothly under reduced pressure of less than 0.1 MPa. Furthermore, the reaction may be performed under increased pressure within a range in which the raw materials do not liquefy.

There is no limitation on the reaction time. For example, the contact time represented by W/F0, i.e., the ratio of the amount of packed catalyst W(g) to the total flow rate F0 (a flow rate at 0° C. and 0.1 MPa: cc/sec) of gas components supplied to the reaction system is preferably about 0.1 to 90 g·sec/cc, and more preferably about 1 to 50 g·sec/cc. In this case, the total flow rate of gas components means the total flow rate of the chloropropene intermediate and hydrogen fluoride, and, when used, inert gas, oxygen, etc.

In step (d), the product obtained in the first stage may be supplied to the reactor of step (d) as is, but is preferably supplied to the reactor of step (d) after removing hydrogen chloride contained in the product. Due to this, the effects of reducing energy loss caused by handling hydrogen chloride that is unnecessary in step (d) and improving the selectivity of the desired HFO-1234yf can be expected. The method for removing hydrogen chloride from the product obtained in the first stage is not particularly limited. For example, hydrogen chloride can be easily removed as a column top fraction by distillation of step (e) after step (d).

A reaction mixture containing the desired HFO-1234yf as a main component and also containing the unreacted chloropropene intermediate and the unreacted hydrogen fluoride is obtained by performing step (d) described above. The reaction mixture also contains hydrogen chloride (HCl) produced as a by-product in the reaction in addition to HFO-1234yf, etc.

In step (e), the reaction mixture obtained in step (d) is subjected to distillation. The distillation can be performed using a commonly used distillation column or the like. By this distillation, the mixture can be separated into a first stream comprising HFO-1234yf as a main component and a second stream comprising the unreacted hydrogen fluoride and organic matter containing at least the unreacted chloropropene intermediate as main components. The portion of the distillation column from which the second stream is withdrawn may be the still of the distillation column or a middle portion of the distillation column. The "organic matter containing at least the unreacted chloropropene intermediate" in the second stream contains generally 90% or more chloropropene intermediate and less than 10% of other organic compounds. Examples of other organic compounds include 1233zd (1-chloro-3,3,3-trifluoropropene), 1223xd (1,2-dichloro-3,3,3-trifluoropropene), and the like.

The first stream contains the desired HFO-1234yf as a main component and also contains other components such as hydrogen chloride and 1,1,1,2,2-pentafluoropropane (hereinafter referred to as "245cb") produced as a by-product in the reaction of step (d). The obtained HFO-1234yf can be further subjected to a crude purification step and a fine purification step to yield a final product. Specific methods for the crude purification step and the fine purification step are not particularly limited. For example, water washing, dehydration (drying), distillation, liquid-liquid separation or other means can be applied to the steps.

The distillation described above is performed under conditions in which the unreacted hydrogen fluoride and organic matter containing the unreacted chloropropene intermediate that form the second stream do not undergo liquid-liquid separation.

Examples of the method for performing distillation under conditions in which liquid-liquid separation does not occur include a method in which the molar ratio of the hydrogen fluoride relative to 1 mole of the organic matter in the distillation column, i.e., the [the number of moles of the hydrogen fluoride]/[the number of moles of the organic matter] value, more specifically the [the number of moles of the hydrogen fluoride]/[the number of moles of the unreacted chloropropene intermediate] value is adjusted. The molar ratio can be adjusted by additionally supplying or withdrawing the chloropropene intermediate and/or hydrogen fluoride to or from the distillation column or other lines. In this case, the pressure in the distillation column is not particularly limited and may be, for example, 0 to 1 MPa.

Another method for performing distillation under conditions in which liquid-liquid separation does not occur is, for example, a method in which the pressure in the distillation column is adjusted. For instance, the pressure in the distillation column can be adjusted by changing the temperature in the distillation column. Alternatively, the pressure in the distillation column can be adjusted by supplying the reaction mixture, hydrogen fluoride, and/or others, such as inert gas, to the distillation column or discharging the reaction mixture, hydrogen fluoride, and/or others, such as inert gas.

The occurrence of liquid-liquid separation in the distillation column can be determined from the liquid density of a stream withdrawn from the still of the distillation column. Specifically, when liquid-liquid separation occurs at a portion of the distillation column from which the second stream is withdrawn, an organic layer (layer containing the starting material), which is a lower layer, is mainly withdrawn from the distillation column; therefore, the liquid density of the stream withdrawn from the distillation column is higher than when liquid-liquid separation does not occur, and becomes a value close to the liquid density of the starting material alone. When such a change in the liquid density is observed, it can be determined that liquid-liquid separation has occurred.

As described above, distillation is performed under conditions in which the chloropropene intermediate and the hydrogen fluoride do not undergo liquid-liquid separation, and the second stream containing the chloropropene intermediate and the hydrogen fluoride is withdrawn from the distillation column. If the second stream is withdrawn from the still of the distillation column, the still may be, for example, heated to 33° C. or more since liquid-liquid separation is much less likely to occur. The temperature of the still is particularly preferably 50° C. or more.

More specifically, conditions for the distillation can be set as follows.

First, the pressure in the distillation column in which the distillation of step (e) is performed is defined as $Y_2$ (MPa; gauge pressure), the molar ratio of the hydrogen fluoride relative to 1 mole of the organic matter (i.e., [the number of moles of the hydrogen fluoride]/[the number of moles of the organic matter]) is defined as $X_2$, and the relationship between $X_2$ and $Y_2$ is plotted. The organic matter here means the chloropropene intermediate. The relationship between $X_2$ and $Y_2$ (10 to 50 points) are plotted in the same ranges as in the distillation in the first stage. By plotting in such a manner, an X—Y curve is drawn, from which a relational expression that expresses $Y_2$ as a function of $X_2$ is calculated. Automated calculation software may be used to calculate this relational expression.

If the relational expression is expressed as $f(X_2)$, as long as the relationship of $Y_2 \geq f(X_2)$ is satisfied, the distillation can be performed under conditions in which liquid-liquid separation does not occur. Thus, the molar ratio $X_2$ and the pressure in the distillation column $Y_2$ can be adjusted so as to satisfy this relationship to perform the distillation.

Figure 2:
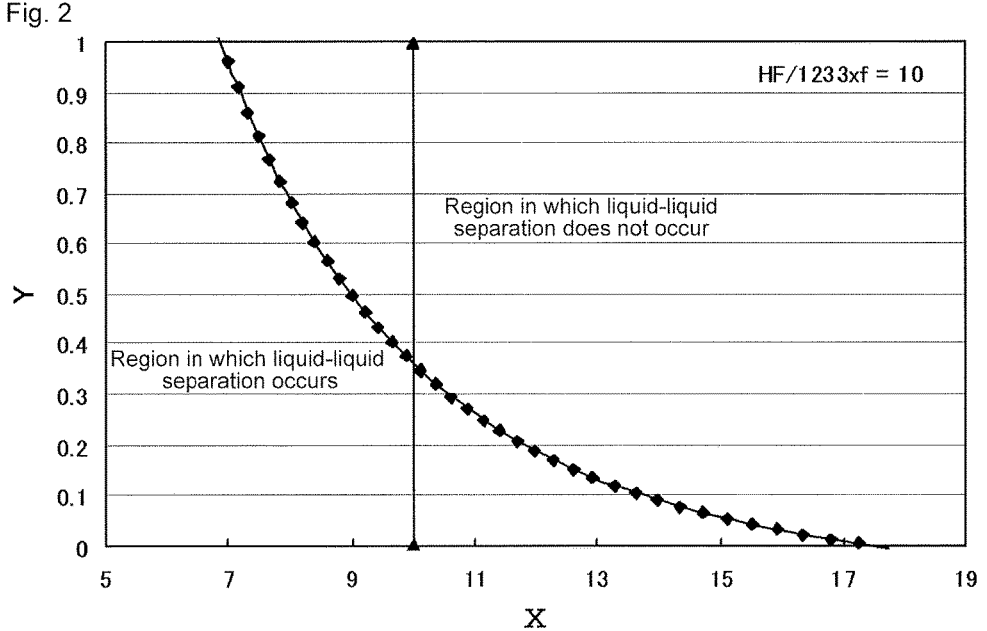
FIG. 2 is a liquid-liquid separation curve plotting the pressure in the distillation column versus the hydrogen fluoride/chloropropene intermediate molar ratio.

FIG. 2 is a curve (liquid-liquid separation curve) derived from the relationship between $Y_2$ and $X_2$ by using the above method when the chloropropene intermediate is 2-chloro-3,3,3-trifluoropropene. If the chloropropene intermediate is 2-chloro-3,3,3-trifluoropropene, the relationship between $Y_2$ and $X_2$ is derived from the liquid-liquid separation curve shown in FIG. 2 to obtain the following equation (1).

$$Y_2 \geq -0.00004X_2^5 + 0.0026X_2^4 - 0.0653X_2^3 + 0.8224X_2^2 - 5.3282X_2 + 14.787 \quad (1)$$

When the chloropropene intermediate is 2-chloro-3,3,3-trifluoropropene, liquid-liquid separation of the hydrogen fluoride and the organic matter containing the chloropropene intermediate can be prevented by determining $X_2$ and $Y_2$ and performing distillation in such a manner that the relationship of equation (1) is satisfied. In particular, deactivation of the catalyst is further suppressed in the region in FIG. 2 in which $X \geq 10$ and $Y_2 \geq f(X_2)$.

In step (f), the second stream withdrawn from the distillation column is fed to the reactor where the reaction of step (d) is performed. Thus, the chloropropene intermediate and the hydrogen fluoride can be recycled to the reaction of step (d). For example, the second stream can be fed to the rector while pressure is applied with a pump, a compressor, or the like.

As described above, withdrawing the second stream without occurrence of liquid-liquid separation in the distillation of step (e) prevents a high concentration of the chloropropene intermediate in the second stream, resulting in suppression of deactivation of the catalyst used in the reaction of step (d). If liquid-liquid separation into two phases occurs, the lower phase is the chloropropene intermediate, which has a greater specific gravity. Thus, if the second stream in a state in which liquid-liquid separation occurs is withdrawn, the chloropropene intermediate is fed in a high concentration to the reactor. If the amount of the organic matter such as the chloropropene intermediate is too large in the reaction system, the catalyst tends to be covered with the organic matter, leading to deactivation of the catalyst. However, withdrawing the second stream without occurrence of liquid-liquid separation in step (e) prevents a high concentration of the chloropropene intermediate from being fed to the reactor, making deactivation of the catalyst unlikely to occur. This enables HFO-1234yf to be stably produced for a long period of time.

HFO-1234yf can also be produced by using the first stage and the second stage in combination. Specifically, the chloropropene intermediate of formula (II) can be produced from a starting material containing the compound of formula (Ia) and/or the compound of formula (Ib) in the first stage, and then, HFO-1234yf can be produced, in the second stage, from the chloropropene intermediate obtained in the first stage.

Also when HFO-1234yf is produced by using the first stage and the second stage in combination as described above, the first stage comprises step (a), step (b), and step (c) mentioned above, and the second stage comprises step (d), step (e), and step (f) mentioned above.

The distillation of step (b) is performed under conditions in which the unreacted starting material and the unreacted hydrogen fluoride do not undergo liquid-liquid separation, or the distillation of step (e) is performed under conditions in which the unreacted hydrogen fluoride and the organic matter containing the unreacted chloropropene intermediate do not undergo liquid-liquid separation. Alternatively, the distillation of step (b) is performed under conditions in which the unreacted starting material and the unreacted hydrogen fluoride do not undergo liquid-liquid separation, and the distillation of step (e) is performed under conditions in which the unreacted hydrogen fluoride and the organic matter containing the unreacted chloropropene intermediate do not undergo liquid-liquid separation. This makes deactivation of the catalyst unlikely to occur in the first stage and/or the second stage, enabling the chloropropene intermediate of the first stage and HFO-1234yf of the second stage to be stably produced for a long period of time.

FIG. 1 is a schematic flow diagram illustrating an example of the flow for the production of HFO-1234yf. In the production flow of FIG. 1, HFO-1234yf is produced in a production line comprising a first reactor 1a, a second reactor 1b, a first distillation column 2a, a second distillation column 2b, and the like. The reaction of step (a) in the first stage can be performed in the first reactor 1a, and the reaction of step (d) in the second stage can be performed in the second reactor 1b.

More specifically, the starting material is supplied from the inlet side 10a of the first reactor 1a together with hydrogen fluoride to allow a reaction to proceed in the presence of a catalyst. Subsequently, the reaction products are withdrawn from the outlet side 11a of the first reactor 1a. The reaction mixture containing a chloropropene intermediate as a product, the unreacted starting material chloropropane, and the unreacted hydrogen fluoride is supplied to the first distillation column 2a where step (b) is performed.

In the first distillation column 2a, the chloropropene intermediate as a product is withdrawn as a first stream from the top 20a of the first distillation column 2a and is supplied to the second reactor 1b. The unreacted starting material chloropropane and the unreacted hydrogen fluoride are withdrawn as a second stream from the still 21a of the first distillation column 2a and are supplied to the first reactor 1a to be reused for the reaction of step (a). As described above, the distillation is performed under conditions in which the unreacted starting material and the unreacted hydrogen fluoride do not undergo liquid-liquid separation.

The chloropropene intermediate supplied to the second reactor 1b is reacted with hydrogen fluoride in the presence of a catalyst. The hydrogen fluoride used here may be separately supplied to the second reactor 1b. Subsequently, the reaction products are withdrawn from the outlet side 11b of the second reactor 1b. The reaction mixture containing the desired HFO-1234yf as a main component and also containing the unreacted chloropropene intermediate and the unreacted hydrogen fluoride is supplied to the second distillation column 2b where step (e) is performed.

HFO-1234yf supplied to the second distillation column 2b is withdrawn from the top 20b of the second distillation column 2b by distillation. The hydrogen chloride and the like are then removed by purification or like treatment. The chloropropene intermediate and the unreacted hydrogen fluoride are withdrawn from the still 21b of the second distillation column 2b and are supplied to the second reactor 1b to be reused for the reaction of step (d). As described above, the distillation is performed under conditions in which the unreacted chloropropene intermediate and the unreacted hydrogen fluoride do not undergo liquid-liquid separation. The production flow mentioned above is an example for producing HFO-1234yf, and HFO-123.4yf may be produced in a production line other than that shown in FIG. 1.

EXAMPLES

Examples are given below to illustrate the present invention in more detail; however, the present invention is not limited to these Examples.

Example 1

According to the production flow shown in FIG. 1, HFO-1234yf was produced. Cylinder-shaped reactors made of Hastelloy C22 were used. Cylinder-shaped packed columns made of Hastelloy C22 were used as distillation columns. The packing used was CMRNo2.5, the column diameter was 500 A, and the packed length was 10000 mm×2.

240db (1,1,1,2,3-pentachloropropane) was used as a starting material in step (a) of the first stage. A mixed gas of 240db and hydrogen fluoride was continuously supplied to a first reactor 1a at a flow rate of 7,000 m$^3$/hr (in terms of standard conditions for gas). The internal temperature of the first reactor 1a was 300° C., and the pressure was 0.75 MPa (gauge pressure). Further, in the reaction, the molar ratio of hydrogen fluoride to 240db was 20. To the first reactor 1a, 24.8 t of a Cr oxide catalyst ($Cr_2O_3$) was supplied as a catalyst in advance.

After the reaction, the reaction products were withdrawn from the first reactor 1a, fed to a first distillation column 2a, and subjected to distillation. The unreacted 240db and the unreacted hydrogen fluoride were withdrawn from the still of the first distillation column 2a and fed to the first reactor 1a again to be reused as raw materials for the reaction. From the top of the first distillation column 2a, 1233xf (2-chloro-3,3,3-trifluoropropene) as a product was withdrawn and fed to a second reactor 1b where the reaction of the next second stage was performed. In the reaction, the conversion of 240db to 1233xf was 50 to 99%.

Figure 3:
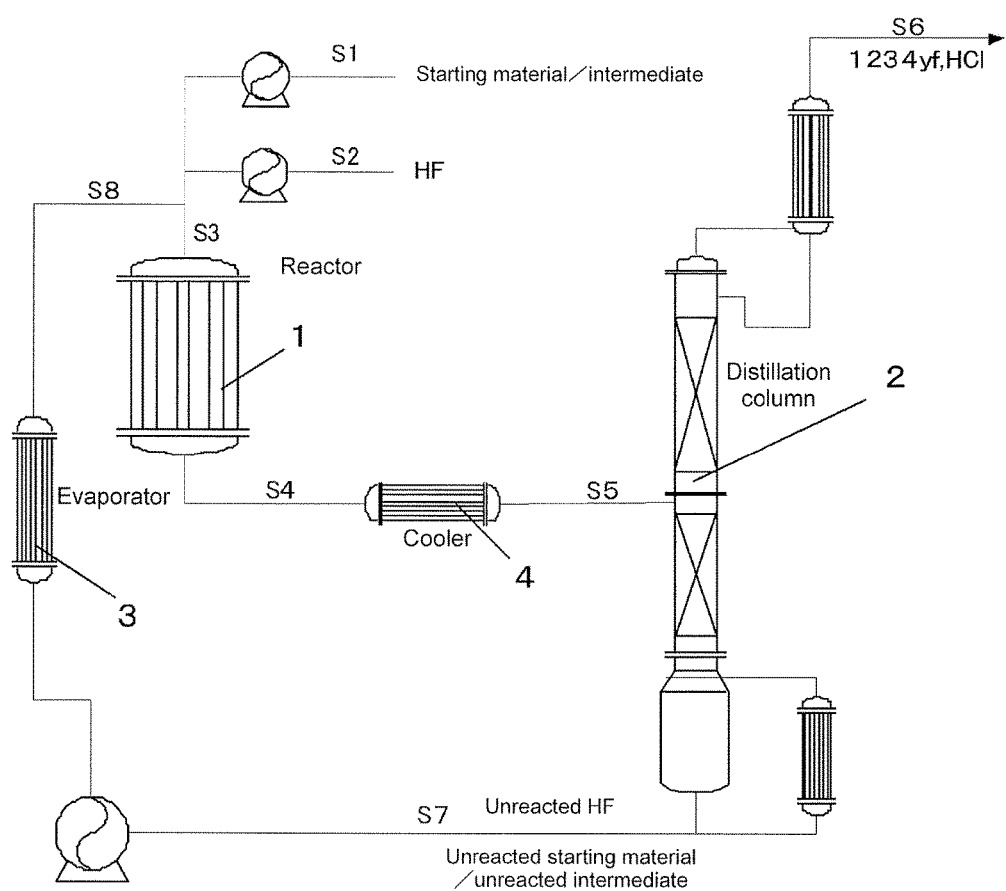
FIG. 3 is a flow diagram illustrating an example of the method for producing 2,3,3,3-tetrafluoropropene and is a schematic flow diagram illustrating the recycling process from the distillation column to the reactor.

FIG. 3 is a schematic flow diagram illustrating the process from reaction to distillation in more detail. The materials of the evaporator 3 and the cooler 4 shown in FIG. 3 were Hastelloy C22 in this Example.

1233xf was fed through the S1 line of FIG. 3 from the first distillation column 2a, hydrogen fluoride was supplied from the S2 line, and these two came together in the S3 line. The mixed gas of 1233xf and hydrogen fluoride was continuously supplied to a reactor 1 through the S3 line at a flow rate of 21,000 m$^3$/hr (in terms of standard conditions for gas). In the reactor 1, 1233xf was reacted with hydrogen fluoride in the presence of 49.6 t of a Cr oxide catalyst ($Cr_2O_3$) used as a catalyst. The internal temperature of the reactor 1 was 365° C., and the pressure was 0.75 MPa (gauge pressure). Further, in this reaction, the molar ratio of hydrogen fluoride to 1233xf was 10. After the reaction, the obtained reaction mixture was fed from the reactor 1 to a distillation column 2. In the reaction in the reactor 1, 1,1,1,2,2-pentafluoropropane (245cb) was produced as a by-product.

The distillation in the distillation column 2 was performed under the following conditions: a column top temperature of 33° C., a column bottom temperature of 70° C., a pressure of 0.75 MPa, and a reflux ratio of 3.4. The reflux ratio here means the molar flow ratio of reflux liquid to distillate (reflux liquid/distillate). A mixture containing HCl and the desired HFO-1234yf was withdrawn from the top of the column, and a mixture containing the unreacted hydrogen fluoride and the unreacted 1233xf was withdrawn from the still (the bottom of the column). For the distillation, the molar ratios of hydrogen fluoride and 1233xf flown in the S1, S2, and S7 lines of FIG. 3, the flow rates, and the pressure were adjusted so that hydrogen fluoride and 1233xf were maintained in the state of a single phase without liquid-liquid separation in the distillation column 2. The mixture containing the unreacted hydrogen fluoride and the unreacted 1233xf withdrawn from the still was recycled in the second reactor.

Table 1 shows the flow rates of gases in each of the S1 to S8 lines in FIG. 3.

TABLE 1

| | Example 1 | | | | | | | |
|---|---|---|---|---|---|---|---|---|
| | S1 | S2 | S3 | S4 | S5 | S6 | S7 | S8 |
| HF [kmol/hr] | 0 | 0.34 | 12 | 11.76 | 11.76 | 0.10 | 11.66 | 11.66 |
| HCl [kmol/hr] | 0 | 0 | 0 | 0.24 | 0.24 | 0.24 | 0 | 0 |
| 1234yf [kmol/hr] | 0 | 0 | 0 | 0.24 | 0.24 | 0.24 | 0 | 0 |
| 1233xf [kmol/hr] | 0.25 | 0 | 1.2 | 0.96 | 0.96 | 0.01 | 0.95 | 0.95 |
| 245cb [kmol/hr] | 0 | 0 | 0 | 0.04 | 0.04 | 0.04 | 0 | 0 |
| Total flow rate [kmol/hr] | 0 | 0.34 | 13.2 | 13.24 | 13.24 | 0.63 | 12.61 | 12.61 |

Example 2

According to the production flow shown in FIG. 3, 1233xf was produced from 240db. First, 240db was fed through the S1 line, hydrogen fluoride was fed through the S2 line, and these two came together in the S3 line. The mixed gas of 240db and hydrogen fluoride was continuously supplied to a reactor 1 at a flow rate of 7,000 m$^3$/hr (in terms of standard conditions for gas). The internal temperature of the reactor 1 was 300° C., and the pressure was 0.75 MPa (gauge pressure). Further, in this reaction, the molar ratio of hydrogen fluoride to 240db was 20. To the reactor 1, 24.8 t of a Cr oxide catalyst ($Cr_2O_3$) was supplied as a catalyst in advance. After the reaction, the reaction mixture was withdrawn from the reactor 1, fed to a distillation column 2, and subjected to distillation. The same reactor, distillation column, evaporator, and cooler as used in Example 1 were used for the reactor 1, distillation column 2, evaporator 3, and cooler 4.

The distillation in the distillation column 2 was performed under the following conditions: a column top temperature of 6.63° C., a column bottom temperature of 93.6° C., a pressure of 0.75 MPa, and a reflux ratio of 5. A mixture containing 1233xf was withdrawn from the top of the column, and a mixture containing the unreacted hydrogen fluoride and the unreacted 240db was withdrawn from the still (the bottom of the column). The unreacted 240db and unreacted hydrogen fluoride withdrawn from the still were fed to the reactor 1 again to be reused as raw materials for the reaction. For the distillation, the molar ratios of hydrogen fluoride and 240db flown in the S1, S2, and S7 lines of FIG. 3, the flow rates, and the pressure were adjusted so that hydrogen fluoride and 240db were maintained in the state of a single phase without liquid-liquid separation in the distillation column 2.

Table 2 shows the flow rates of gases in each of the S1 to S8 lines in FIG. 3.

TABLE 2

|  | Example 2 | | | | | | | |
|---|---|---|---|---|---|---|---|---|
|  | S1 | S2 | S3 | S4 | S5 | S6 | S7 | S8 |
| HCl [kmol/hr] | 0 | 0 | 0 | 4.09 | 4.09 | 4.09 | 0 | 0 |
| HF [kmol/hr] | 0 | 8.42 | 40.49 | 37.42 | 37.42 | 5.35 | 32.07 | 32.07 |
| 1233xf [kmol/hr] | 0 | 0 | 0.14 | 1.16 | 1.16 | 1.02 | 0.14 | 0.14 |
| 240db [kmol/hr] | 1.02 | 0 | 2.04 | 1.02 | 1.02 | 0 | 1.02 | 1.02 |
| Total flow rate [kmol/hr] | 1.02 | 8.42 | 42.67 | 43.69 | 42.69 | 10.46 | 33.23 | 33.23 |

Example 3

According to the production flow shown in FIG. 3, 1233xf was produced from 1230xa (1,1,2,3-tetrachloropropene). First, 1230xa was fed through the S1 line, hydrogen fluoride was fed through the S2 line, and these two came together in the S3 line. The mixed gas of 1230xa and hydrogen fluoride was continuously supplied to a reactor 1 at a flow rate of 7,000 m$^3$/hr (in terms of standard conditions for gas). The internal temperature of the reactor 1 was 300° C., and the pressure was 0.75 MPa. Further, in this reaction, the molar ratio of hydrogen fluoride to 1230xa was 20. To the reactor 1, 24.8 t of a Cr oxide catalyst ($Cr_2O_3$) was supplied as a catalyst in advance. After the reaction, the reaction mixture was withdrawn from the reactor 1, fed to a distillation column 2, and subjected to distillation. The unreacted 1230xa and the unreacted hydrogen fluoride were withdrawn from the still of the distillation column 2 and fed to the reactor 1 again to be reused as raw materials for the reaction. The same reactor, distillation column, evaporator, and cooler as used in Example 1 were used for the reactor 1, distillation column 2, evaporator 3, and cooler 4.

The distillation in the distillation column 2 was performed under the following conditions: a column top temperature of −13.2° C., a column bottom temperature of 89.6° C., pressure of 0.75 MPa, and a reflux ratio of 4. A mixture containing 1233xf was withdrawn from the top of the column, and a mixture containing the unreacted hydrogen fluoride and the unreacted 1230xa was withdrawn from the still (the bottom of the column). For the distillation, the molar ratios of hydrogen fluoride and 1230xa flown in the S1, S2, and S7 lines of FIG. 3, the flow rates, and the pressure were adjusted so that hydrogen fluoride and 1230xa were maintained in the state of a single phase without liquid-liquid separation in the distillation column 2.

Table 3 shows the flow rates of gases in each of the S1 to S8 lines in FIG. 3.

TABLE 3

|  | Example 3 | | | | | | | |
|---|---|---|---|---|---|---|---|---|
|  | S1 | S2 | S3 | S4 | S5 | S6 | S7 | S7 |
| HCl [kmol/hr] | 0 | 0 | 0 | 4.97 | 4.97 | 4.97 | 0 | 0 |
| HF [kmol/hr] | 0 | 6.76 | 33.18 | 28.21 | 28.21 | 1.79 | 26.42 | 26.42 |
| 1233xf [kmol/hr] | 0 | 0 | 0.12 | 1.77 | 1.77 | 1.66 | 0.12 | 0.12 |
| 1230xa [kmol/hr] | 1.66 | 0 | 1.67 | 0.01 | 0.01 | 0 | 0.01 | 0.01 |
| Total flow rate [kmol/hr] | 1.66 | 6.76 | 34.96 | 34.96 | 34.96 | 8.41 | 26.55 | 26.55 |

Example 4

According to the production flow shown in FIG. 3, 1233xf was produced from 243db (2,3-dichloro-1,1,1-trifluoropropane). First, 243db was fed through the S1 line, hydrogen fluoride was fed through the S2 line, and these two came together in the S3 line. The mixed gas of 243db and hydrogen fluoride was continuously supplied to a reactor 1 at a flow rate of 7,000 m$^3$/hr (in terms of standard conditions for gas). The internal temperature of the reactor 1 was 300° C., and the pressure was 0.75 MPa. Further, in this reaction, the molar ratio of hydrogen fluoride to 243db was 20. To the reactor 1, 24.8 t of a Cr oxide catalyst ($Cr_2O_3$) was supplied as a catalyst in advance. After the reaction, the reaction mixture was withdrawn from the reactor 1, fed to a distillation column 2, and subjected to distillation. The same reactor, distillation column, evaporator, and cooler as used in Example 1 were used for the reactor 1, distillation column 2, evaporator 3, and cooler 4.

The distillation in the distillation column 2 was performed under the following conditions: a column top temperature of 1.24° C., a column bottom temperature of 81.1° C., a pressure of 0.75 MPa, and a reflux ratio of 5. A mixture containing 1233xf was withdrawn from the top of the column, and a mixture containing the unreacted hydrogen fluoride and the unreacted 243db was withdrawn from the still (the bottom of the column). The unreacted 243db and unreacted hydrogen fluoride withdrawn from the still were fed to the reactor 1 again to be reused as raw materials for the reaction. For the distillation, the molar ratios of hydrogen fluoride and 243db flown in the S1, S2, and S7 lines of FIG. 3, the flow rates, and the pressure were adjusted so that hydrogen fluoride and 243db were maintained in the state of a single phase without liquid-liquid separation in the distillation column 2.

Table 4 shows the flow rates of gases in each of the S1 to S8 lines in FIG. 3.

TABLE 4

| | Example 4 | | | | | | | |
|---|---|---|---|---|---|---|---|---|
| | S1 | S2 | S3 | S4 | S5 | S6 | S7 | S8 |
| HCl [kmol/hr] | 0 | 0 | 0 | 1.95 | 1.95 | 1.95 | 0 | 0 |
| HF [kmol/hr] | 0 | 2.36 | 33.38 | 33.06 | 33.06 | 1.04 | 32.02 | 32.02 |
| 1234yf [kmol/hr] | 0 | 0 | 0 | 0.32 | 0.32 | 0.32 | 0 | 0 |
| 245cb [kmol/hr] | 0 | 0 | 0.19 | 0.19 | 0.19 | 0 | 0.19 | 0.19 |
| 1233xf [kmol/hr] | 0 | 0 | 1.57 | 2.88 | 2.88 | 1.31 | 1.57 | 1.57 |
| 243db [kmol/hr] | 1.63 | 0 | 1.64 | 0.01 | 0.01 | 0 | 0.01 | 0.01 |
| Total flow rate [kmol/hr] | 1.63 | 2.36 | 36.78 | 38.41 | 38.41 | 4.62 | 33.79 | 33.79 |

Example 5

According to the production flow shown in FIG. 3, 1233xf was produced from 244bb (2-chloro-1,1,1,2-tetrafluoropropane). First, 244bb was fed through the S1 line, and a mixed gas of this 244bb and hydrogen fluoride was continuously supplied to a reactor 1 at a flow rate of 7,000 m$^3$/hr (in terms of standard conditions for gas). In this reaction, hydrogen fluoride was released from 244bb used as a raw material; therefore, hydrogen fluoride was not supplied from the S2 line. The internal temperature of the reactor 1 was 300° C., and the pressure was 0.75 MPa. Further, in this reaction, the molar ratio of hydrogen fluoride to 244bb was 20. To the reactor 1, 0.75 MPa 24.8 t was supplied as a catalyst in advance. After the reaction, the reaction mixture was withdrawn from the reactor 1, fed to a distillation column 2, and subjected to distillation. The same reactor, distillation column, evaporator, and cooler as used in Example 1 were used for the reactor 1, distillation column 2, evaporator 3, and cooler 4.

The distillation in the distillation column 2 was performed under the following conditions: a column top temperature of 6.63° C., a column bottom temperature of 93.6° C., a pressure of 0.75 MPa, and a reflux ratio of 4. A mixture containing 1233xf was withdrawn from the top of the column, and a mixture containing the unreacted hydrogen fluoride and the unreacted 244bb was withdrawn from the still (the bottom of the column). The unreacted 244bb and unreacted hydrogen fluoride withdrawn from the still were fed again to the reactor 1 to be used as raw materials for the reaction. For the distillation, the molar ratios of hydrogen fluoride and 244bb flown in the S1, S2, and S7 lines of FIG. 3, the flow rates, and the pressure were adjusted so that hydrogen fluoride and 244bb were maintained in the state of a single phase without liquid-liquid separation in the distillation column 2.

Table 5 shows the flow rates of gases in each of the S1 to S8 lines in FIG. 3.

TABLE 5

| | Example 5 | | | | | | | |
|---|---|---|---|---|---|---|---|---|
| | S1 | S2 | S3 | S4 | S5 | S6 | S7 | S8 |
| HCl [kmol/hr] | 0 | 0 | 0 | 1.19 | 1.19 | 1.19 | 0 | 0 |
| HF [kmol/hr] | 0 | 0 | 8.10 | 12.17 | 12.17 | 4.07 | 8.10 | 8.10 |
| 1234yf [kmol/hr] | 0 | 0 | 0 | 1.19 | 1.19 | 1.19 | 0 | 0 |
| 1233xf [kmol/hr] | 0 | 0 | 0.27 | 4.34 | 4.34 | 4.07 | 0.27 | 0.27 |
| 244bb [kmol/hr] | 5.25 | 0 | 5.65 | 0.40 | 0.40 | 0 | 0.40 | 0.40 |
| Total flow rate [kmol/hr] | 5.25 | 0 | 14.02 | 19.27 | 19.27 | 10.50 | 8.77 | 8.77 |

Comparative Example

Under the same conditions as in Example 1, 1233xf was produced from 240db by the reaction of the first stage. Subsequently, the obtained 1233xf was withdrawn from the top of a first distillation column 2a and fed to a second reactor 1b where the reaction of the second stage was performed. More specifically, according to the production flow shown in FIG. 3, 1233xf was fed through the S1 line, hydrogen fluoride was supplied through the S2 line, and these two came together in the S3 line. The mixed gas of 1233xf and hydrogen fluoride was continuously supplied to a reactor 1 through the S3 line at a flow rate of 21,000 m$^3$/hr (in terms of standard conditions for gas). In the reactor 1, 1233xf was reacted with hydrogen fluoride in the presence of 49.6 t of a Cr oxide catalyst ($Cr_2O_3$) used as a catalyst. The internal temperature of the reactor 1 was 365° C., and the pressure was 0.1 MPa (gauge pressure). Further, in this reaction, the molar ratio of hydrogen fluoride to 1233xf was 10, and W/F0 was 10. After the reaction, the obtained reaction mixture was fed from the reactor 1 to a distillation column 2.

The distillation in the distillation column 2 was performed under the following conditions: a column top temperature of 33° C., a column bottom temperature of 70° C., a pressure of 0.1 MPa, and a reflux ratio of 3.4. A mixture containing HCl and the desired HFO-1234yf was withdrawn from the top of the column, and a mixture containing the unreacted hydrogen fluoride and the unreacted 1233xf was withdrawn from the still. For the distillation, the molar ratios of hydrogen fluoride and 1233xf flown in the S1, S2, and S7 lines of FIG. 3, the flow rates, and the pressure were adjusted so that hydrogen fluoride and 1233xf underwent liquid-liquid separation in the distillation column 2. The mixture containing the unreacted hydrogen fluoride and unreacted 1233xf withdrawn from the still was recycled in the second reactor.

Deactivation of Catalyst

Figure 4:
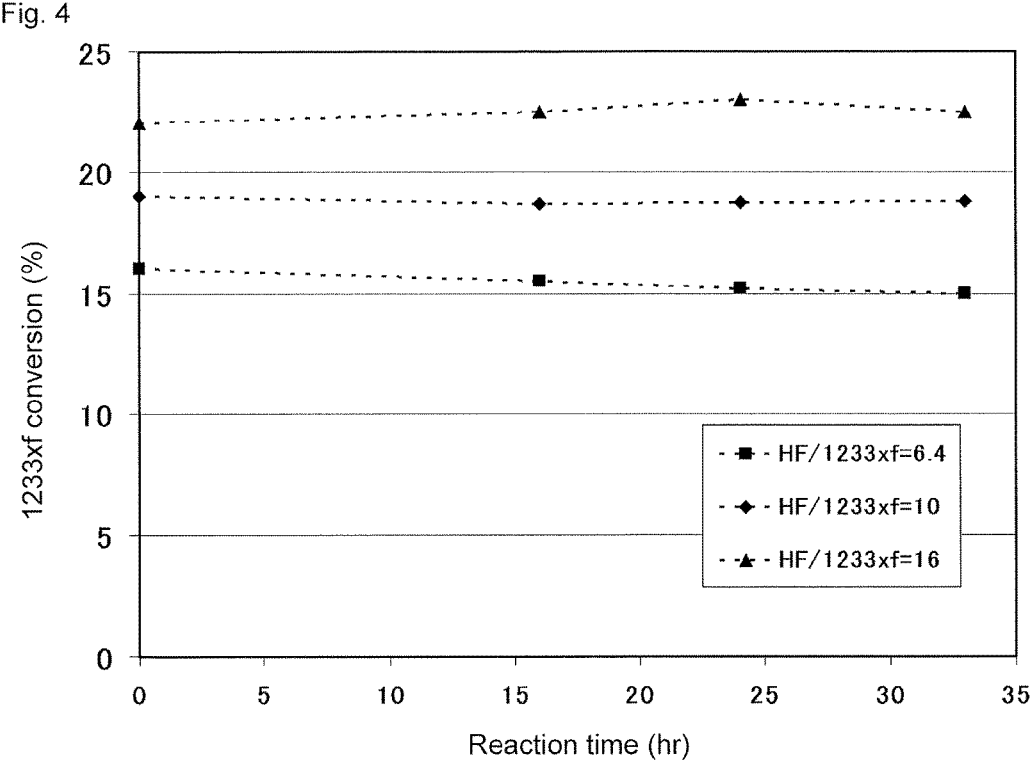
FIG. 4 is a graph plotting the conversion of 1233xf versus the reaction time.

FIG. 4 is a graph plotting the relationship between the conversion of 1233xf to 1234yf and the reaction time in Example 1. FIG. 4 also shows results obtained in the case in which the molar ratio of hydrogen fluoride to 1233xf in the reaction of the second stage of Example 1 was changed to 6.4 and in the case in which the molar ratio of hydrogen fluoride to 1233xf in the reaction of the second stage of Example 1 was changed to 16 (the pressure in the distillation column in both cases was 0.75 MPa). This graph indicates that when the molar ratio was 6.4, which is a condition that does not satisfy equation (1) described above (see also FIG. 2), the catalyst was deactivated, resulting in low conversion, and the conversion further decreased with the reaction time. In contrast, when the molar ratio was 10 or 16, which are conditions that satisfy equation (1) (see also FIG. 2), deactivation of the catalyst was suppressed, resulting in high conversion, and the degree of a decrease in the conversion was suppressed in spite of elapse of the reaction time compared with the case in which the molar ratio was 6.4.

Figure 5:
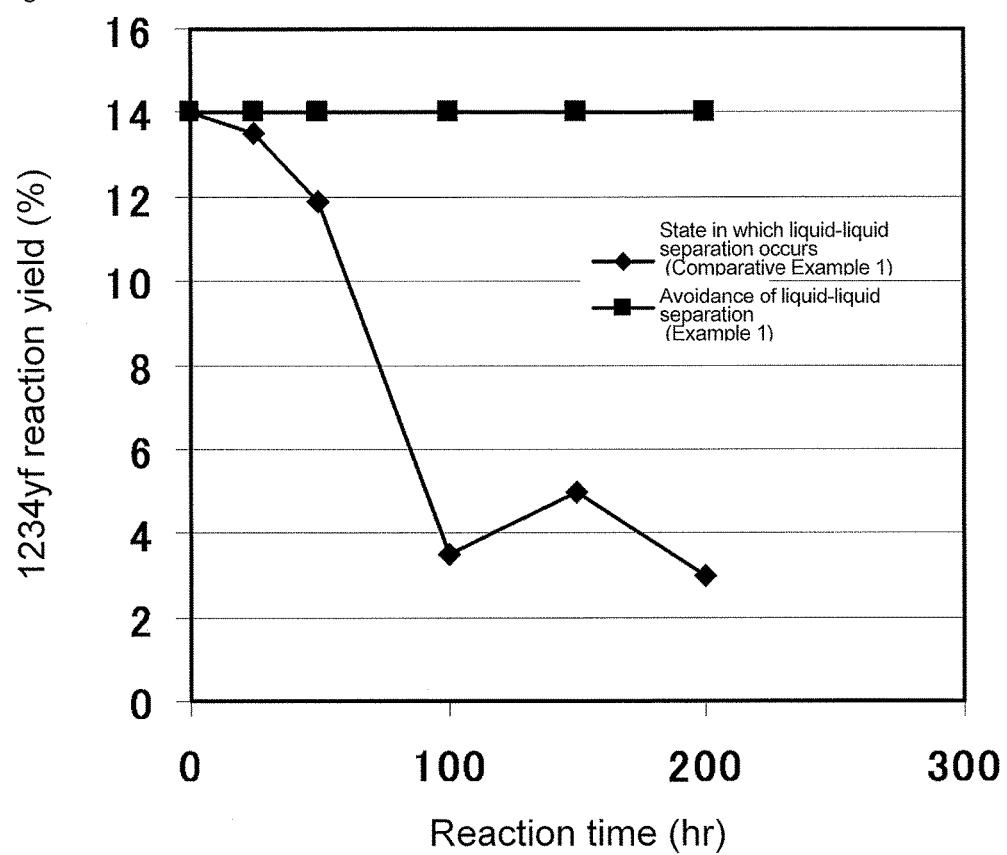
FIG. 5 is a graph plotting the reaction yield of 1234yf versus the reaction time.

FIG. 5 is a graph plotting the relationship between the reaction time and the reaction yield of HFO-1234yf in the reaction of the second stage of Example 1 and plotting the relationship between the reaction time and the reaction yield of HFO-1234yf in the reaction of the Comparative Example. In the Comparative Example, the reaction yield decreased with elapse of the reaction time. In contrast, in Example 1, a decrease in the reaction yield was not observed even 200 hours after the start of the reaction. Since the distillation was performed under conditions in which hydrogen fluoride and 1233xf underwent liquid-liquid separation in Comparative Example, a large amount of organic matter was returned to the reactor when reflux was performed. Thus, the catalyst was deactivated by the action of the organic matter, causing a decrease in the reaction yield. In contrast, in Example 1, the distillation was performed under conditions in which hydrogen fluoride and 1233xf did not undergo liquid-liquid separation; therefore, even though reflux was performed, deactivation of the catalyst was unlikely to occur, enabling the reaction to be stably performed for a long period of time.

DESCRIPTION OF REFERENCE NUMERALS

1 Reactor
1a First reactor
1b Second reactor
2 Distillation column
2a First distillation column
2b Second distillation column
3 Evaporator
4 Cooler

The invention claimed is:

1. A method for producing a chloropropene represented by formula (II): $CX_3CCl=CH_2$, wherein at least one X is F and the other or others are Cl or F, and each X may be the same or different, from a starting material containing a chloropropane represented by formula (Ia): $CX_3CClYCH_2Y$, wherein X is Cl or F and each X may be the same or different, Y is H, F, or Cl and each Y may be the same or different and/or a chloropropene represented by formula (Ib): $CY_3CCl=CZ_2$, wherein Y is H or Cl and each Y may be the same or different, and Z is H, F, or Cl and each Z may be the same or different, the method comprising the following steps (a) to (c):
   (a) reacting the starting material with hydrogen fluoride in the presence of a catalyst;
   (b) subjecting the reaction mixture obtained in step (a) to distillation to separate the mixture into a first stream comprising the chloropropene of formula (II) as a main component and a second stream comprising unreacted starting material and unreacted hydrogen fluoride as main components; and
   (c) recycling the second stream separated in step (b) to the reaction of step (a),
   the distillation of step (b) being performed under conditions in which the unreacted starting material and the unreacted hydrogen fluoride do not undergo liquid-liquid separation at a portion of a distillation column from which the second stream is withdrawn, the conditions being established by heating to 33° C. or more the portion of the column from which the second stream is withdrawn, and withdrawing the second stream therefrom.

2. The method according to claim 1, wherein in the distillation of step (b), the molar ratio of the hydrogen fluoride to the starting material is 15 or more, and the pressure in the distillation column where the distillation of step (b) is performed is 0 MPa or more but 1 MPa or less.

* * * * *